United States Patent [19]

Roshdy

[11] 4,427,109

[45] Jan. 24, 1984

[54] CENTERING FOLDER RETAINER FOR NEEDLED SUTURES

[75] Inventor: Constance E. Roshdy, North Brunswick, N.J.

[73] Assignee: Ethicon, Inc., Somerville, N.J.

[21] Appl. No.: 500,463

[22] Filed: Jun. 2, 1983

[51] Int. Cl.³ .............................................. A61L 15/00
[52] U.S. Cl. .................................. 206/63.3; 206/476; 206/484; 206/628
[58] Field of Search ...................... 206/63.3, 438, 476, 206/477, 482–484, 488, 489, 491, 492, 498; 229/88

[56] References Cited

U.S. PATENT DOCUMENTS

| | | | |
|---|---|---|---|
| 3,876,068 | 4/1975 | Sonnino | 206/63.3 |
| 3,939,969 | 2/1976 | Miller et al. | 206/63.3 |
| 4,249,659 | 2/1981 | Cerwin et al. | 206/63.3 |
| 4,253,563 | 3/1981 | Komarnycky | 206/63.3 |
| 4,284,194 | 8/1981 | Flatau | 206/63.3 |

*Primary Examiner*—Joseph Man-Fu Moy
*Attorney, Agent, or Firm*—Robert L. Minier

[57] ABSTRACT

An improved multi-panel suture retainer. The retainer provides separate compartments for the needle and the suture material. The suture material is disposed within the retainer inwardly from all edges of the retainer to better protect heat sensitive suture materials during subsequent sterilization and packaging.

8 Claims, 7 Drawing Figures

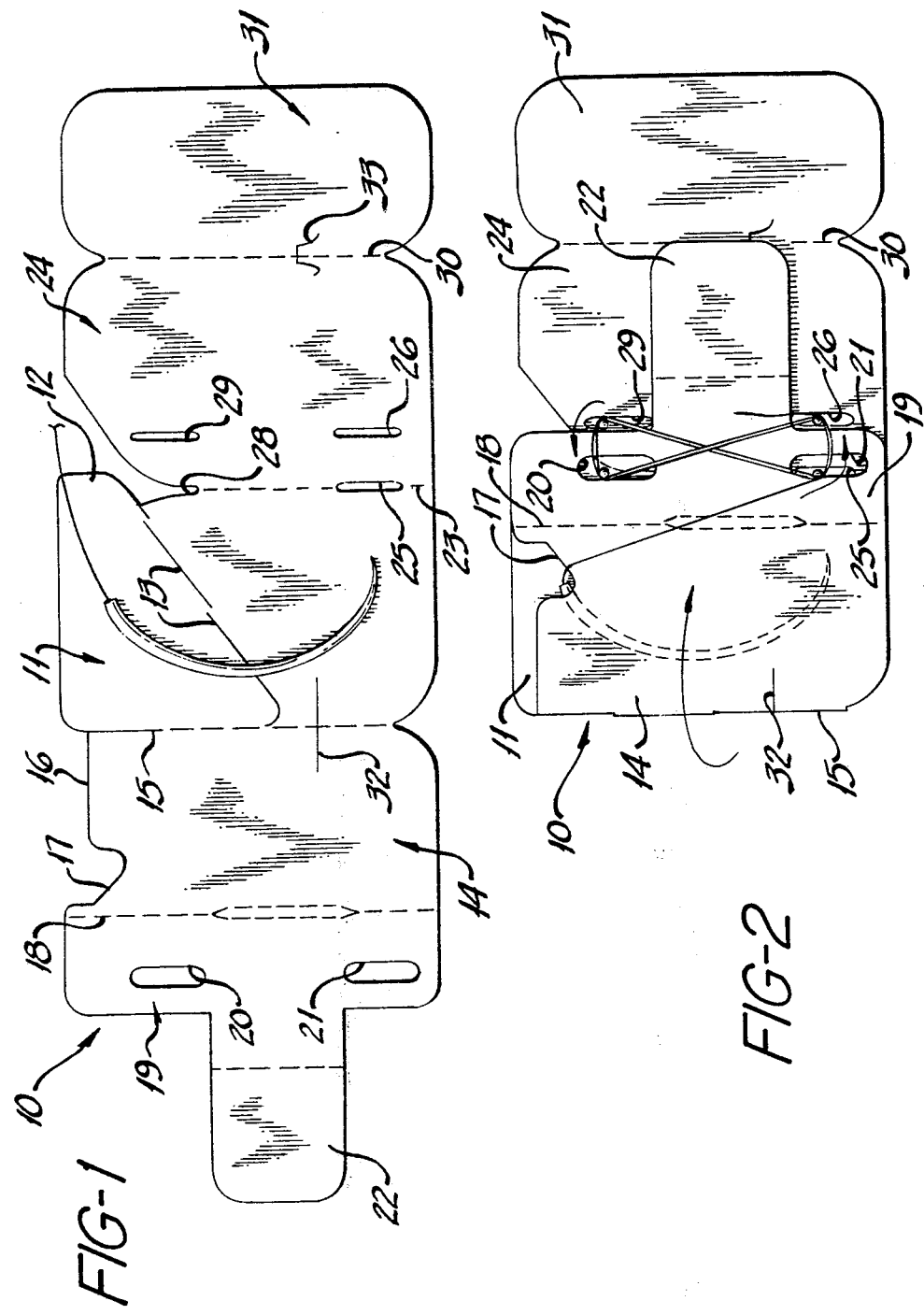

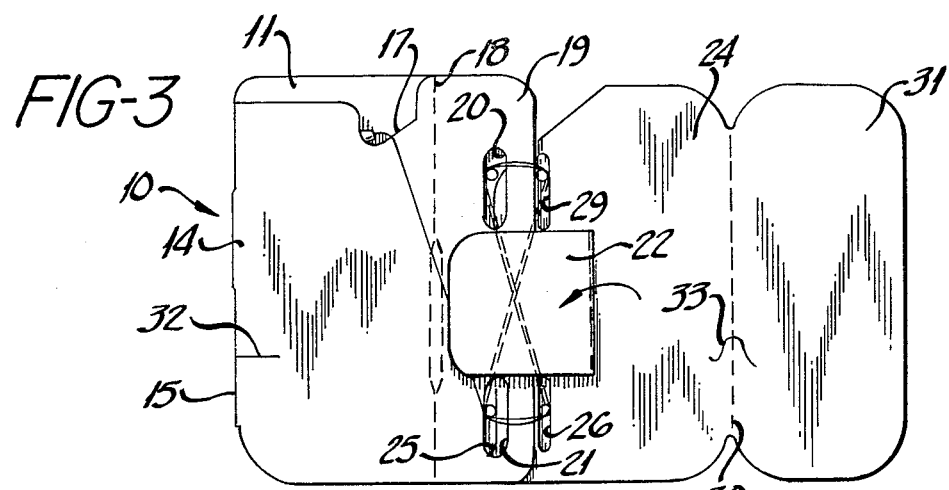
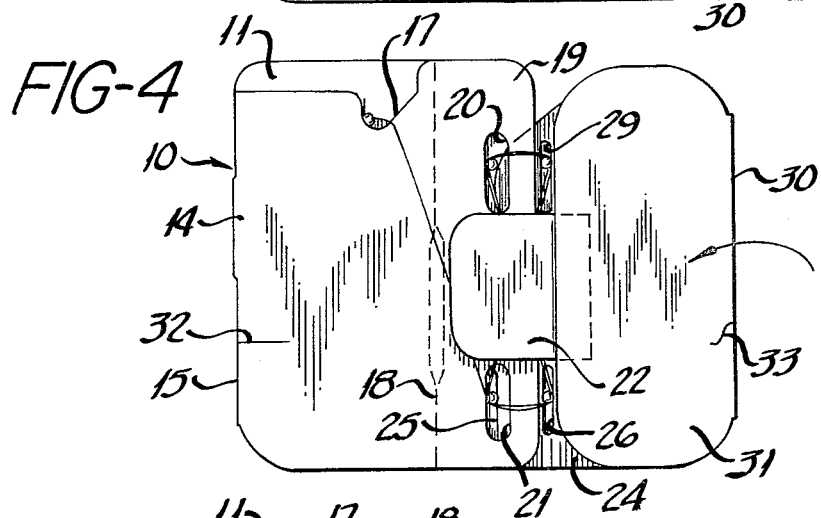
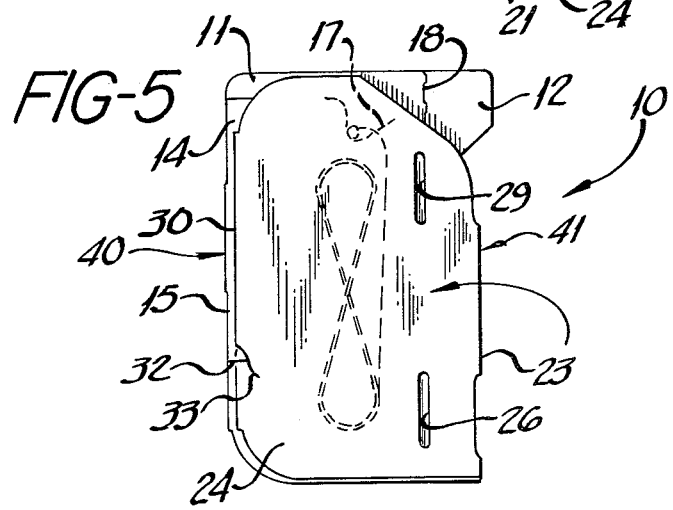

CENTERING FOLDER RETAINER FOR NEEDLED SUTURES

BACKGROUND OF THE INVENTION

In the past, suture retainers in many configurations have been provided to aid in the handling of suture material during sterilization and packaging and/or to retain the suture in a specific configuration to facilitate dispensing of the suture from the suture package. Sutures within such retainers are sterilized and further packaged in a heat sealed outer package which maintains the suture's sterility. U.S. Pat. Nos. 3,939,969 and 4,249,656 disclose suture retainers which aid in the handling, sterilization, and dispensing of the sutures contained therein, and which may be contained in a heat sealed outer package.

Suture retainers, as shown in U.S. Pat. Nos. 4,249,656 and 3,444,994 often are provided with holes or openings to receive suture winding pins so that the suture may be wound within the retainer. Suture materials secured within a retainer with pin holes remain exposed to the environment through the pin holes and often are subject to degradation from environmental conditions; for example, heat, light, humidity and specifically, the heat in the heat sealing process very often used to heat seal and form the outer sterile package. In commonly assigned co-pending Patent application Ser. No. 273,804 filed June 15, 1981, there is disclosed a package which protects a suture from being exposed to undesirable environmental conditions through the pin holes by providing a sliding panel which covers the pin holes when the retainer is finally folded.

In packaging suture materials, including needled sutures, where the suture material is subject to degradation from environmental conditions, it is desirable to protect the suture material from the undesirable environmental conditions to which it might be exposed when forming the final package. The package should have the needle and the suture material separated so that no damage can be done to one by the other. Also, for economic and manufacturing means, the package should be usable with various size needles and suture materials. The package should be constructed so as to be usable with suture materials which have a lot of spring or memory and tend to spring away from a tightly wound configuration.

What I have discovered is a suture retainer which maintains the needle and the suture material attached thereto separate to reduce damage caused to one by the other. In my improved retainer, I can package various sized needles and I can package suture material which has a lot of spring or memory. My new retainer protects the suture material from being degraded especially by heat during subsequent sterilization and packaging of the retainer. Other objects of the present invention will become readily apparent from the following detailed description.

SUMMARY OF THE INVENTION

The present invention provides a multi-panel suture retainer which, in its folded configuration, provides a separate compartment for a needle attached to the suture material and a separate compartment for the suture material. The suture retainer further protects the suture material from degradation due to exposure by disposing the suture material inwardly from all edges of the suture retainer so that the suture material is disposed away from any further heat sealing when the retainer is placed in a suitable heat sealed sterile package. The improved retainer of the present invention comprises first and second needle retainer panels. These panels have a generally rectangular shape and are foldably connected to each other at a common longitudinal edge. A suture winding panel is foldably connected to the second needle retainer panel along the longitudinal edge opposite the edge connected to the first needle retainer panel. The suture winding panel has two suture winding holes disposed therein and these holes are spaced inwardly from the edges of said panel. A suture retainer panel is foldably connected to the suture winding panel along the edge opposite the edge connected to the second needle retainer panel. The width of the suture winding panel is less than the width of the second needle retainer panel. The width of the second needle retainer panel is likewise less than the width of the first needle retainer panel. My improved suture retainer includes first and second suture protector panels with each panel having a generally rectangular shape. The first suture protector panel is foldably connected to the first needle retainer panel. It is connected along the longitudinal edge opposite the edge connected to the second needle retainer panel. Two suture winding holes are disposed in the foldably connected edge between the first needle retainer panel and the first suture protector panel. The holes are aligned so as to underlie the holes in the suture winding panel when the second needle retainer panel and the suture winding panel are folded on top of the first needle retainer panel. The width of the first suture protector panel is substantially equal to the width of the first needle retainer panel. The second suture protector panel is foldably connected to the first suture protector panel along the longitudinal edge opposite the longitudinal edge connected to the first needle retainer panel. The width of the second suture protector panel is less than the width of the first suture protector panel. When a needled suture is packaged in the retainer and the retainer folded according to the present invention, the needle is retained in one compartment and the suture retained in a separate compartment. The suture is disposed inwardly from the edges of the folded retainer and the protector panels protect the suture from being exposed through the openings in the suture winding panel.

BRIEF DESCRIPTION OF THE DRAWINGS

The invention will be more fully described when taken in conjunction with the accompanying drawings wherein:

FIG. 1 is a plan view of an unfolded suture retainer of the present invention with a needle positioned in the unfolded retainer;

FIG. 2 is a plan view of the retainer of FIG. 1 illustrating the folding to form the needle retaining compartment and depicting the suture being wound about appropriate pins;

FIG. 3 is a plan view of the retainer of FIG. 2 folded so that the wound suture is retained;

FIG. 4 is a plan view of the retainer of FIG. 3 with the suture protecting panels folded about the wound suture;

FIG. 5 is a plan view of the fully folded suture retainer of FIG. 4;

DETAILED DESCRIPTION OF THE PRESENT INVENTION

Figure 6:
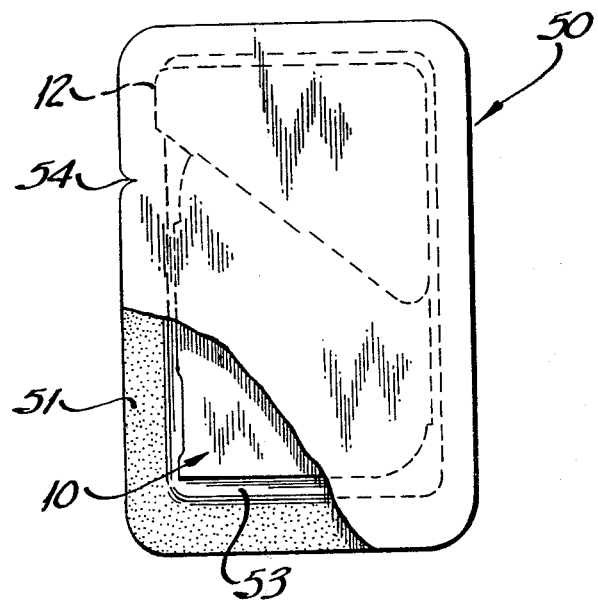
FIG. 6 is a plan view of the fully folded suture retainer of FIG. 5 contained within a sealed outer envelope.
Figure 7:
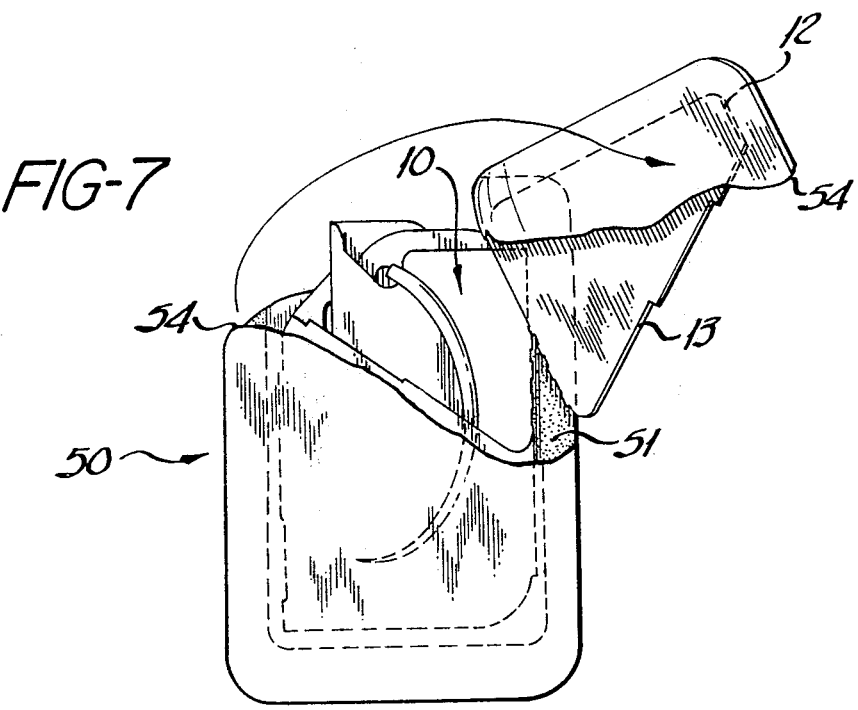
FIG. 7 is a plan view of the subject package and envelope of FIG. 6 opened to provide access to the needle and suture.

In the various figures of the suture retainer of the present invention shown in the accompanying drawings, the same number for the panels is used throughout the drawings including FIGS. 6 and 7 wherein the retainer of the previous figures has been packaged in an appropriate heat-sealed container.

The retainer 10 of FIG. 1 comprises a first needle retainer panel 11. The first needle retainer panel is the widest panel of all panels in the retainer. The first needle retainer panel has a tab 12 extending from one corner and a die/cut diagonal portion 13 extending across the width of the panel. The tabs and diagonal die cut are used for providing easy access to the needle as will be hereinafter described with FIGS. 6 and 7. A second needle retainer panel 14, which is also generally rectangular in shape, is foldably connected along one longitudinal edge 15 of the first needle retainer panel. The second needle retainer panel is not quite as long as the first needle retainer panel and along its upper edge 16 there is disposed a cutout area 17. Foldably connected to the longitudinal edge 18 of this said second needle retainer panel is a suture winding panel 19. The suture winding panel has two suture winding panel has two suture winding holes 20 and 21 disposed within the panel. In this embodiment the holes are generally oblong in shape and are disposed inwardly from the transverse edges of the panel. Attached to this suture winding panel is a suture retainer panel 22. The width of the suture retainer panel and the width of the suture winding panel are both less than the width of the second needle retainer. The reason for these width relationships will be more fully appreciated after the full description of the folded retainer is provided.

Attached to the opposite longitudinal edge 23 of the first needle retainer panel is a first suture protector panel 24. This suture protector panel has disposed in its surface a pair of holes 25 and 26 through which winding pins may be placed. Also, on the foldably connected line 23 between the first needle retainer panel and the first suture protector panel there are openings 28 and 29 through which winding pins may also be placed. Foldably connected to the free longitudinal edge 30 of this first suture protector panel is a second suture protector panel 31. This second suture protector panel is also generally rectangular in shape. On the foldably connected line 15 between the first and second needle retainer panels there is a die cut slit 32 and on the foldably connected line 30 between the first and second suture protector panels there is a complementary die cut slit 33. These slits are for locking all of the panels together after the retainer has been completely folded as will be described hereinafter.

In using the retainer of the present invention, the suture retainer is placed on appropriate pins which extend through the openings on the connecting line between the first needle retainer panel and the first suture protector panel. A needle is placed on the first suture retaining panel as illustrated in FIG. 1. The second needle retainer 14 along with the suture winding panel 19 and the suture retaining panel 22 is folded over on the foldable line between the first and second needle retainer panels as shown in FIG. 2. This places the needle in the compartment formed between the first and second needle retainer panels and the openings in the suture winding panel are placed over the winding pins. At this point the suture is carried through the depression 17 in the second needle retainer panel and is wound about the pins. In this embodiment the suture is wound in a figure-8 configuration as shown. As can be seen, the suture when wound is disposed inwardly from the outside transverse edges 40 and 41 of the retainer.

Referring to FIG. 3 the suture retainer panel 22 is folded back over on to the suture to retain the suture in its figure-8 configuration. Referring to FIG. 4 the second suture protector panel is folded on top of the first suture protector panel enclosing a portion of the suture winding panel and the suture retainer panel between the two suture protector panels. As shown in FIG. 5 the first suture protector panel is then folded about the foldably connected line between that panel and the first needle retainer panel. As this is accomplished the suture winding panel is simultaneously folded about its foldably connected line to the second needle retainer panel. This folding causes the panels 19 and 24 to slide across each other and cover the openings in the panels to prevent suture material from being exposed through the openings. As shown in FIG. 5 the suture is disposed within the folded retainer in a manner so that it is disposed inwardly from all edges of the folded retainer.

The die cut portions 32 and 33 along the foldably connected line between the first and second needle retainer panels and the first and second suture protector panels may then be interengaged to lock all the panels together.

In the embodiment depicted in FIGS. 1 through 5 the foldably connected line 18 between the second needle retainer panel and the suture winding panel is a double line to form a gusset therebetween. Such a double folded line provides some depth to the suture material compartment to aid in preventing any damage to the suture due to increased pressure, etc. and to provide depth to the compartment to assist in removing the suture from the compartment. It should be appreciated that other fold lines could also have the double fold or gusset configuration.

The suture retainer with the needle and suture therein may then be packaged and sterilized by various techniques as is well known in the art. In FIGS. 6 and 7 a specific package is shown. This is a conventional suture package 50 formed by heat sealing the periphery 51 of two panels of aluminum foil coated on the interior surfaces thereof with a heat sealable polymeric composition. Other means for sealing may be employed as desired. Disposed within the envelope is the fully folded retainer of FIG. 5 with the needled suture therein. The entire package has been sterilized. The tab 12 projects slightly beyond the width of the folded retainer and is secured in the sealed area 53 of the envelope. A tear notch 54 is provided in the outer edge of the envelope and located approximately at the lower edge of the tab to facilitate opening of the suture package when tearing the outer envelope. A suture package illustrated in FIG. 6 is sterile and hermetically sealed and may be stored for extended periods of time. When the suture is to be removed from the package, the outer envelope is opened by tearing at the notch as illustrated in FIG. 7. Since the tab is secured at the seal line of the envelope about the notch, the first needle retainer panel is simultaneously torn at the die cut areas 13 as the envelope is opened. This tearing exposes the end of the needle with the suture attached thereto and it is a simple matter to grasp the needle with an appropriate needle holder and remove the needled suture from the package.

As may be appreciated, because the suture is totally enclosed by the retainer and there are no portions exposed through openings or otherwise to the environment and because the suture is also disposed inwardly from all of the edges of the retainer the suture is well protect from being overheated and, hence, degraded when sealed in the hermetically heat sealed package described in conjunction with FIGS. 6 and 7.

The suture retainer of the present invention may be constructed of a heavyweight relatively stiff paper or paper board such as 5 to 12 point solid, bleached, sulfate board. The paper board is foldable and yet sufficiently strong and stiff to support the suture and provide a relatively rigid package. Similar materials including plastic, foils and laminates of these with each other or with paper can also be used with good results. The suture retainer can be readily cut from such materials by a single die which also forms the desired fold lines including the necessary gussets in accordance with the present invention.

Sutures packaged in accordance with the present invention may be multifilament or monofilament sutures and they may be braided, twisted or covered.

The preceding description has been directed primarily to preferred embodiments of the present invention and many variations which nevertheless employ the essential features thereof may be apparent to those skilled in the art.

What is claimed is:

1. A needled suture retainer comprising:

first and second needle retainer panels, said panels each having a generally rectangular shape and said panels being foldably connected to each other at a common longitudinal edge, a suture winding panel, said panel having two suture winding holes disposed inwardly from the edges of said panel and said panel foldably connected to the second needle retainer panel along the longitudinal edge opposite the longitudinal edge connected to the first needle retainer panel, a suture retainer panel foldably connected to the suture winding panel along the edge opposite the edge connected to the second needle retainer panel, the width of the suture winding panel being less than the width of the second needle retainer panel and the width of said second needle retainer panel being less than the width of the first needle retainer panel, first and second suture protector panels, each panel having a generally rectangular shape, said first suture protector panel foldably connected to the first needle retainer panel along the longitudinal edge opposite the longitudinal edge connected to the second needle retainer panel, two suture winding holes disposed in the foldably connected edge between the first needle retainer panel and the first suture protector panel, said holes being disposed so as to underlie the holes in the suture winding panel when the second needle retainer panel and the suture winding panel are folded on top of the first needle retainer panel, said second suture protector panel foldably connected to the first suture protector panel along the longitudinal edge opposite the longitudinal edge and connected to the first needle retainer panel, the width of said second suture protector panel being less than the width of said first suture protector panel whereby a needled suture, when packaged in said retainer and said retainer is folded the needle and suture are retained in separate compartments and the suture is disposed inwardly from the edges of said folded retainer.

2. A retainer according to claim 1 having integral locking means to secure said retainer in its folded configuration.

3. A retainer according to claim 2 wherein the integral locking means are interlocking tabs disposed at the foldable edge between the first and second needle retainer panels and the foldable edge between the first and second suture protector panels.

4. A retainer according to claim 1 including dual parallel fold lines between the second needle retainer panel and the suture winding panel.

5. A retainer according to claim 1 wherein the width of the first suture protector panel is substantially equal to the width of the first needle retainer panel.

6. A suture package comprising a combination of a folded retainer of claim 1 or 2 with a needled suture positioned therein enclosed in an outer envelope, said outer envelope being heat sealed around the periphery thereof.

7. A suture package comprising a folded suture retainer of claim 1 or 2 with a needled suture retained therein in separate compartments within said retainer and including layers of materials on opposite sides of said retainer and being heat sealed about the periphery thereof to form a hermetically sealed package for said retainer and the needled suture therein.

8. The package of claim 7 wherein the layers are aluminum foil coated with a heat sealable material.

* * * * *